US00PP20796P2

(12) United States Plant Patent
Fleischle

(10) Patent No.: US PP20,796 P2
(45) Date of Patent: Mar. 2, 2010

(54) ***STREPTOCARPUS* PLANT NAMED 'ROULETTE CHERRY'**

(50) Latin Name: *Streptocarpus×hybridus Voss*
Varietal Denomination: Roulette Cherry

(75) Inventor: Achim Fleischle, Vaihingen/Enz (DE)

(73) Assignee: Fleischle Gartenbau GbR, Vaihingen/Enz (DE)

( * ) Notice: Subject to any disclaimer, the term of this patent is extended or adjusted under 35 U.S.C. 154(b) by 0 days.

(21) Appl. No.: 12/150,589

(22) Filed: Apr. 29, 2008

(51) Int. Cl.
*A01H 5/00* (2006.01)

(52) U.S. Cl. ..... Plt./333

(58) Field of Classification Search ..... Plt./333
See application file for complete search history.

*Primary Examiner*—June Hwu
(74) *Attorney, Agent, or Firm*—Mark P. Bourgeois

(57) ABSTRACT

A new cultivar of *Streptocarpus* plant named 'Roulette Cherry' that is characterized by large leaves, large flowers and flowers with a white center and throat and red outer lobes.

1 Drawing Sheet

Botanical classification: *Streptocarpus×hybridus Voss.*
Variety denomination: 'Roulette Cherry'.

BACKGROUND OF THE INVENTION

The present invention relates to a new and distinct cultivar of *Streptocarpus* plant botanically known as *Streptocarpus* and hereinafter referred to by the cultivar name 'Roulette Cherry'.

'Roulette Cherry' is a hybrid that originated from a crossing in the June of 2002 of the female or seed parent an unnamed proprietary *Streptocarpus* plant (not patented) and the male or pollen parent an unnamed proprietary *Streptocarpus* plant (not patented). The resulting seeds were subsequently planted and grown. The cultivar 'Roulette Cherry' was selected by the inventor in December of 2002 as a single plant within the progeny of the stated cross in Vaihingen/Enz, Germany.

Asexual reproduction of the new cultivar 'Roulette Cherry' first occurred by leaf cuttings in May of 2003 in Vaihingen/Enz, Germany. Since that time, under careful observation, the unique characteristics of the new cultivar have been uniform, stable and reproduced true to type in successive generations of asexual reproduction.

SUMMARY OF THE INVENTION

The following represent the distinguishing characteristics of the new *Streptocarpus* cultivar 'Roulette Cherry'. These traits in combination distinguish 'Roulette Cherry' as a new and distinct cultivar apart from other existing known varieties of *Streptocarpus.*

1. *Streptocarpus* 'Roulette Cherry' exhibits large flowers.
2. *Streptocarpus* 'Roulette Cherry' exhibits bi-colored flowers with a white center and throat and red outer lobes.
3. *Streptocarpus* 'Roulette Cherry' exhibits large leaves.

The closest comparison cultivars are *Streptocarpus* 'Ambiente' (not patented) and *Streptocarpus* 'Roulette Azur' (U.S. Plant patent application Ser. No. 12/150,554).

'Roulette Cherry' is distinguishable from 'Ambiente' by the following characteristics:

1. 'Roulette Cherry' has larger flowers.
2. 'Roulette Cherry' exhibits bi-colored flowers with a white center and throat and red outer lobes. The flowers of 'Ambiente' are darker red and do not have a white throat.

3. 'Roulette Cherry' has larger leaves than the leaves of 'Ambiente'.
4. 'Roulette Cherry' has longer pedicels.
5. 'Roulette Cherry' exhibits flowers that are more rounded. The flowers of 'Ambiente' are more angular.

'Roulette Cherry' is distinguishable from 'Roulette Azur' by the following characteristics:

1. 'Roulette Cherry' has larger flowers.
2. 'Roulette Cherry' exhibits bi-colored flowers with a white center and throat and red outer lobes. The flowers of 'Roulette Azur' are white with violet margins.
3. 'Roulette Cherry' has larger leaves than the leaves of 'Roulette Azur'.
4. 'Roulette Cherry' has longer pedicels.

'Roulette Cherry' is distinguishable from the unnamed female or seed parent by the following characteristics:

1. 'Roulette Cherry' has bi-colored flowers with lighter red outer lobes.
2. 'Roulette Cherry' has larger leaves.

'Roulette Cherry' is distinguishable from the unnamed male or pollen parent by the following characteristics:

1. 'Roulette Cherry' has bi-colored flowers with white center and throat and red outer lobes. The flowers of the pollen parent are white and are not bi-colored.
2. 'Roulette Cherry' has larger flowers.

BRIEF DESCRIPTION OF THE DRAWING

The accompanying photograph illustrates the distinguishing traits of *Streptocarpus* 'Roulette Cherry'. The plant in the photograph shows an overall view of a 10 week old plant. The photograph was taken using conventional techniques and although colors may appear different from actual colors due to light reflectance it is as accurate as possible by conventional photographic techniques.

BOTANICAL DESCRIPTION OF THE PLANT

The following is a detailed description of the new *Streptocarpus* cultivar named 'Roulette Cherry'. Data was collected in Vaihingen/Enz, Germany from 10 week old glass greenhouse grown plants in 12 cm. diameter containers. The time of year was Winter and the temperature range was 20–22 degrees Centigrade during the day and 18–20 degrees Centigrade at night. The light level was 2000 to 3000 Lux. No photoperiodic treatments or growth retardants were used. Color determinations are in accordance with The Royal Horticultural Society Colour Chart 2007 edition, except where general color terms of ordinary dictionary significance are used. The growing requirements are similar to the species. 'Roulette Cherry' has not been tested under all possible conditions and phenotypic differences may be observed with variations in environmental, climatic, and cultural conditions, however, without any variance in genotype.

Botanical classification: *Streptocarpus* 'Roulette Cherry'.

Use: Indoor plant or ornamental perennial in warmer climates.

Parentage: Hybrid of two unnamed *Streptocarpus* plants.

Vigor: Strong.

Growth habit: Ground hugging, clump forming.

Plant shape: Rounded, clump forming plant with upright leaves.

Suitable container size: 12 cm. pots.

Height: 21 cm. in height.

Width: 35 cm. in width.

Low temperature tolerance: 8° Centigrade.

High temperature tolerance: 30° Centigrade.

Propagation: Leaf cuttings.

Time to initiate roots in summer: 25 days to initiate roots at 24° Centigrade.

Time to initiate roots in winter: 21 days to initiate roots at 22° Centigrade.

Time to produce a rooted cutting or liner in summer: 140 days at 24° Centigrade.

Time to produce a rooted cutting or liner in winter: 135 days at 22° Centigrade.

Crop time: Approximately 8 to 10 weeks.

Root system: Fibrous.

Stem: No stems, Leaves grow directly from base, Average 10 clumps.

Foliage:

- *Texture.*—Only slightly glossy.
- *Leaf arrangement.*—In whorls.
- *Compound or single.*—Single.
- *Leaf shape.*—Obolanceolate.
- *Leaf apex.*—Obtuse.
- *Leaf base.*—Attenuate.
- *Leaf length.*—25.0 cm. in length.
- *Leaf width.*—8.0 cm. in width.
- *Pubescence.*—Upper side coarse and dense, lower side puberulent.
- *Leaf margin.*—Crenulate, undulate.
- *Young leaf color* (*lower surface*).—145B.
- *Young leaf color* (*upper surface*).—N137B.
- *Mature leaf color* (*lower surface*).—145B.
- *Mature leaf color* (*upper surface*).—N137B.
- *Vein color* (*under surface*).—145C.
- *Vein color* (*upper surface*).—145A.
- *Venation pattern.*—Strong midrib with alternating lateral veins.
- *Leaf attachment.*—Petiolate.
- *Petiole dimensions.*—5 cm. in length, and 70 mm. in diameter.
- *Petiole surface texture.*—Pubescent.
- *Petiole color.*—145C.

Flower:

- *Inflorescence arrangement.*—Raceme.
- *Flowering habit.*—Continuous.
- *Quantity of flowers per inflorescence.*—Average 5.
- *Inflorescence dimensions.*—15 cm. in height and 10 cm. in width.
- *Flower type.*—Zygomorph with five petals fused to a conical throat ending in a flaring five lobed corolla disk.
- *Quantity of flowers per lateral stem.*—Average 5.
- *Quantity of flower buds per lateral stem.*—Average 5.
- *Quantity of flowers and buds per plant.*—20.
- *Natural flowering season.*—All year.
- *Fragrance.*—None.
- *Rate of flower opening.*—Within two weeks of visible raceme.
- *Flower bud length.*—5.0 cm.
- *Flower bud diameter.*—2.0 cm. in diameter.
- *Flower bud shape.*—Club shaped.
- *Bud color.*—N155B with a tip 58A.
- *Rate of bud opening.*—2 days.
- *Flower aspect.*—Drooping with corolla disk outward.
- *Flower shape.*—Tubular with flaring corolla disk.
- *Flower dimensions.*—Average 5.8 cm. in diameter and 5.8 cm. in height.
- *Flower longevity.*—4–5 days.
- *Petal texture.*—Velvety, soft.
- *Number of petals.*—5.
- *Fused or unfused.*—Fused.
- *Petal arrangement.*—Fused into a tube.
- *Petal shape.*—Orbicular.
- *Petal margin.*—Crenate.
- *Petal apex.*—Obtuse.
- *Petal length.*—18 mm. in length.
- *Petal width.*—1.8 cm.
- *Petal color when opening* (*upper side*).—NN155D with outer lobes 59A.
- *Petal color when opening* (*under side*).—NN155D with outer lobes 59C.
- *Petal color fully opened* (*upper side*).—NN155D with outer lobes 59A.
- *Petal color fully opened* (*under side*).—NN155D with outer lobes 59C.
- *Petal color fading to.*—Outer lobes to 59A.
- *Throat.*—Tubular, 32 mm. in length, 6 mm. in diameter near base, 10 mm. in diameter at flare, inner color NN155D, outer color NN 155C.
- *Self-cleaning or persistent.*—Self-cleaning.

Sepals:

- *Number of sepals.*—Average 5.
- *Sepal shape.*—Linear.
- *Sepal margin.*—Entire.
- *Sepal apex.*—Acuminate.
- *Sepal base.*—Fused linear.
- *Sepal dimensions.*—7 mm. in length and 2 mm. in width.
- *Young sepal color* (*upper side*).—145A.
- *Young sepal color* (*under side*).—145A.
- *Mature sepal color* (*upper side*).—145A.
- *Mature sepal color* (*under side*).—145A.

Calyx:

- *Calyx shape.*—Crown shaped.
- *Calyx dimensions.*—8 mm. in length and 3 mm. in diameter.

Peduncle:

- *Peduncle length.*—Average 1.75 cm.
- *Peduncle diameter.*—Average 2 mm.
- *Peduncle strength.*—Moderately strong.
- *Peduncle surface texture.*—Pubescent.
- *Peduncle color.*—145A.

Pedicels:

*Pedicel length.*—Average 19 cm.

*Pedicel diameter.*—Average 3 mm.

*Pedicel strength.*—Moderately strong.

*Pedicel surface texture.*—Pubescent.

*Pedicel color.*—145A.

Reproduction organs:

*Stamen number.*—2.

*Anther shape.*—Fused.

*Anther size.*—1 mm.

*Anther color.*—162B.

*Amount of pollen.*—Low.

*Pollen color.*—162B.

*Pistil number.*—1.

*Pistil length.*—3 cm. in length.

*Stigma shape.*—Deltoid, bifurcate.

*Stigma color.*—145C.

*Style length.*—12 mm.

*Style color.*—N155C.

*Ovary color.*—145C.

Fruit:

*Fruit dimensions.*—2.5 cm. in length and 0.5 cm. in diameter.

*Fruit color.*—165A.

Seed:

*Seed dimensions.*—0.3 mm. in length and 0.2 mm. in diameter.

*Seed color.*—165D.

*Quantity of seeds.*—50–60.

Disease resistance: Susceptible to *Streptocarpus* flower mottle virus.

The invention claimed is:

1. A new and distinct variety of *Streptocarpus* plant named 'Roulette Cherry' as described and illustrated.

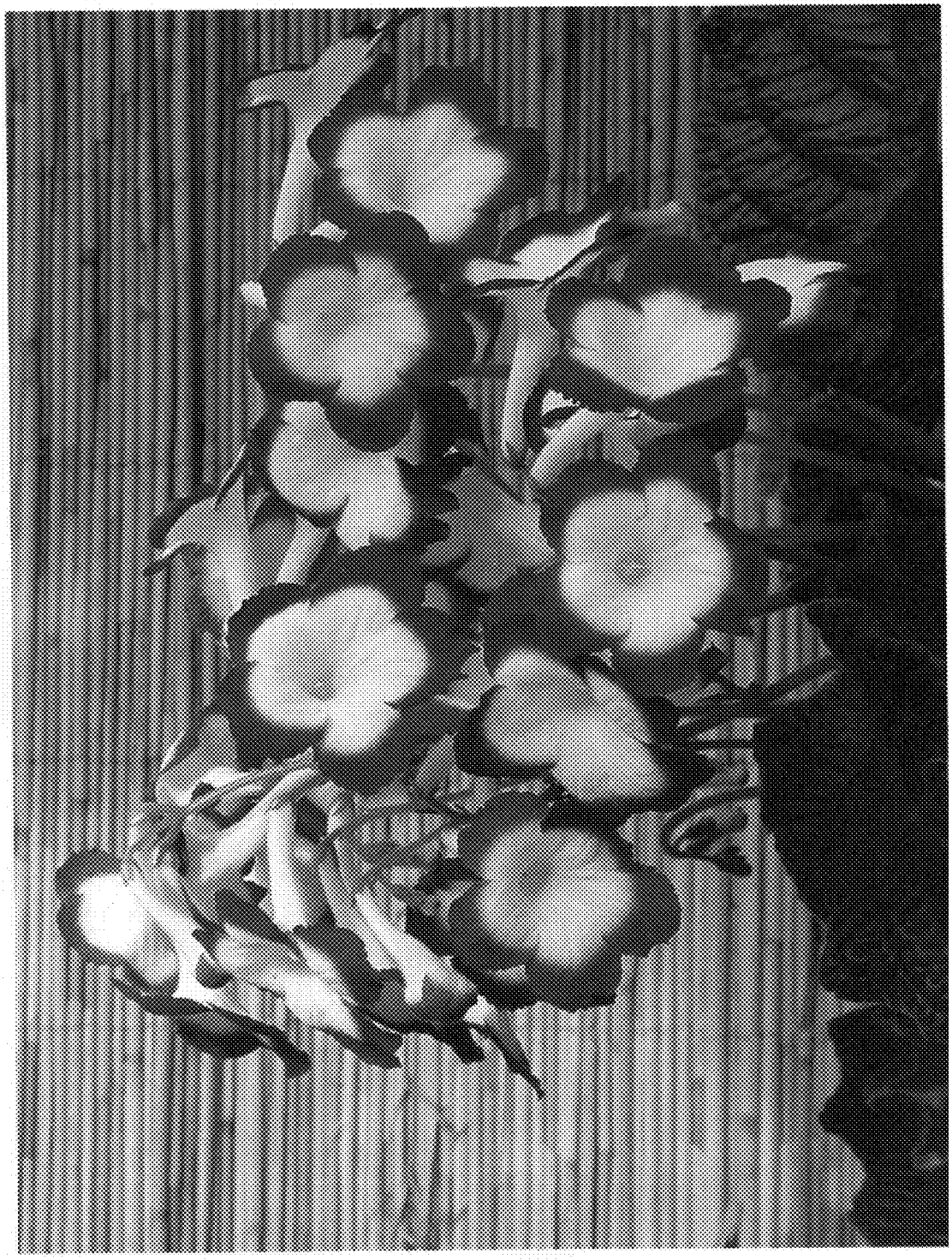

* * * * *